US011350851B2

(12) United States Patent
Chandel et al.

(10) Patent No.: US 11,350,851 B2
(45) Date of Patent: Jun. 7, 2022

(54) WEARABLE APPARATUS AND A METHOD FOR CALCULATING DRIFT-FREE PLANTAR PRESSURE PARAMETERS FOR GAIT MONITORING

(71) Applicant: Tata Consultancy Services Limited, Mumbai (IN)

(72) Inventors: Vivek Chandel, Gurgaon (IN); Shivam Singhal, Gurgaon (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 128 days.

(21) Appl. No.: 16/827,756

(22) Filed: Mar. 24, 2020

(65) Prior Publication Data
US 2020/0305763 A1 Oct. 1, 2020

(30) Foreign Application Priority Data

Mar. 26, 2019 (IN) .............................. 201921011810

(51) Int. Cl.
*A61B 5/103* (2006.01)
*A61B 5/00* (2006.01)
(Continued)

(52) U.S. Cl.
CPC .......... *A61B 5/1038* (2013.01); *A61B 5/6807* (2013.01); *A61B 5/7246* (2013.01);
(Continued)

(58) Field of Classification Search
CPC .................................................. A61B 5/1038
See application file for complete search history.

(56) References Cited

U.S. PATENT DOCUMENTS

2009/0137933 A1* 5/2009 Lieberman ............ A61B 5/1116
600/595
2010/0191153 A1 7/2010 Sanders et al.
(Continued)

FOREIGN PATENT DOCUMENTS

CN 104146712 A 11/2014
WO WO-2018051540 A1 3/2018

OTHER PUBLICATIONS

Bocian, M. et al., "A framework for experimental determination of localised vertical pedestrian forces on full-scale structures using wireless attitude and heading reference systems", Journal of Sound and Vibration, Aug. 18, 2016, pp. 217-243, vol. 376, Elsevier Ltd.

*Primary Examiner* — Hyun D Park
(74) *Attorney, Agent, or Firm* — Finnegan, Henderson, Farabow, Garrett & Dunner, LLP

(57) ABSTRACT

The present disclosure provides wearable apparatus and method for calculating drift-free plantar pressure parameters for gait monitoring of an individual. Most conventional techniques use different kind of sensors placed in in-sole based wearable apparatus but are costly and not effective in calculating accurate plantar pressure parameters. The disclosed wearable apparatus uses off-the shelf piezoelectric sensors that are widely available in market with less cost. The drift-free plantar pressure parameters are calculated using drift-free static pressure data obtained by numerically integrating acquired dynamic sensor data from the piezoelectric sensors, using a LiTCEM correction mechanism. A 6-DOF Inertial Measurement Unit (IMU sensor) helps in isolating zero-pressure duration indicating when a foot of the individual is in air during a stride, while obtaining the drift-free static pressure data. The disclosed wearable appa-
(Continued)

ratus calculate the drift-free plantar pressure parameters for long duration and facilitates monitoring walking patterns of the individual.

20 Claims, 8 Drawing Sheets

(51) Int. Cl.
*G01C 19/00* (2013.01)
*G01L 1/16* (2006.01)
*G01P 7/00* (2006.01)
*G01P 15/02* (2013.01)
*G01P 15/18* (2013.01)

(52) U.S. Cl.
CPC ............... *G01C 19/00* (2013.01); *G01L 1/16* (2013.01); *G01P 7/00* (2013.01); *G01P 15/02* (2013.01); *G01P 15/18* (2013.01); *A61B 2562/0219* (2013.01)

(56) References Cited

U.S. PATENT DOCUMENTS

| | | | |
|---|---|---|---|
| 2011/0054358 A1 | 3/2011 | Kim et al. | |
| 2013/0213147 A1* | 8/2013 | Rice | A43B 3/0005 73/862.046 |
| 2014/0222173 A1* | 8/2014 | Giedwoyn | A43B 3/0005 700/91 |
| 2014/0330171 A1* | 11/2014 | Pan | A61B 5/1123 600/595 |

* cited by examiner

WEARABLE APPARATUS AND A METHOD FOR CALCULATING DRIFT-FREE PLANTAR PRESSURE PARAMETERS FOR GAIT MONITORING

PRIORITY CLAIM

This U.S. patent application claims priority under 35 U.S.C. § 119 to: Indian Patent Application No. 201921011810, filed on 26 Mar. 2019. The entire contents of the aforementioned application are incorporated herein by reference.

TECHNICAL FIELD

The disclosure herein generally relates to healthcare and maintenance of an individual, and particularly to wearable apparatus and a method for calculating drift-free plantar pressure parameters for gait monitoring using off-the shelf piezoelectric sensors.

BACKGROUND

Walking pattern analysis of an individual has become extremely important as health care and maintenance continues to grow with present living conditions. Plantar pressure parameters of the individual play vital role for analyzing the walking patterns which further helps in evaluating Parkinsonian gait, mobility and walking disorders of the individual. Also, the plantar pressure parameters are helpful in evaluating running performance of an athlete. Conventional techniques employ wide variety of sensors for acquiring inputs indicating pressure values of the individual, while moving, to calculate the plantar pressure parameters.

Existing in-sole based solutions for calculating plantar pressure parameters utilize custom made pressure sensors, but they are limited to lab environment based tests and are expensive, resulting in low affordability. Existing in-sole based solutions also employ Force Sensitive Resistors (FSR) which are moderately expensive.

Existing in-sole based solutions also employ piezoelectric sensors for calculating plantar pressure parameters, which are less expensive. However dynamic sensor data acquired by the piezoelectric sensors may exhibit a non-linear force-voltage open circuit response under non-ideal and practical conditions, resulting in a drift. While integrating the acquired dynamic sensor data to obtain static pressure data, the drift is intensified due to hysteresis loss, resulting in inaccurate plantar pressure parameters. Accuracy of the resulted plantar pressure parameters may become worse when the dynamic sensor data is acquired for long duration using the piezoelectric sensors.

SUMMARY

Embodiments of the present disclosure present technological improvements as solutions to one or more of the above-mentioned technical problems recognized by the inventors in conventional systems.

In an aspect, there is provided a wearable apparatus for calculating drift-free plantar pressure parameters for gait monitoring, the apparatus comprising: a footwear input unit comprising a plurality of piezoelectric sensors placed within a sole of a footwear at different positions representing pressure points of a foot and a 6-Degree Of Freedom (DOF) Inertial Measurement Unit (IMU) placed at bottom of the footwear representing a mid-foot area, to acquire raw data samples continuously at a predefined sampling rate, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t; and a processing unit comprising one or more internal data storage devices operatively coupled to one or more hardware processors for storing instructions configured for execution by the one or more hardware processors; wherein the one or more hardware processors are configured to receive each raw data sample and further configured to: extract each group of the raw data samples falling within a predefined time window was a raw sub-data sample, wherein the raw sub-data sample comprises the raw foot pressure values, the raw 3-axis accelerometer values, the raw 3-axis gyroscope values, and the associated timestamp t; identify sub-time windows $(m_1, m_2, m_3 \ldots, m_n)$ within each of the predefined time window w based on a predefined sub-time window duration d, wherein the raw sub-data sample within each of the sub-time windows comprises the raw 3-axis accelerometer values and the raw 3-axis gyroscope values with the associated timestamp t; determine a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll; obtain a static pressure value for each raw foot pressure value acquired by each piezoelectric sensor of the plurality of piezoelectric sensors, each of the raw foot pressure value being comprised in the raw data samples falling within each predefined time window w, by integrating the associated raw foot pressure values; extract a data sample number having a minimum static pressure value present between each pair of consecutive identified sub-time windows that represent the true stride; calculate drift-free static pressure values $(PC_{ij})$ for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers having the minimum static pressure value; and calculate drift-free plantar pressure parameters in terms of a drift-free Vertical Ground Reaction Force (VGRF) and a 2-dimensional Centre of Pressure (CoP) location for each data sample number falling within each predefined time window w.

In another aspect, there is provided a wearable system for calculating drift-free plantar pressure parameters for gait monitoring, the system comprising: a footwear input unit comprising: a plurality of piezoelectric sensors placed within a sole of a footwear at different positions representing pressure points of a foot and a 6-Degree Of Freedom (DOF) Inertial Measurement Unit (IMU) placed at bottom of the footwear representing a mid-foot area, to acquire raw data samples continuously at a predefined sampling rate, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t; and a remote processing unit comprising one or more internal data storage devices operatively coupled to one or more hardware processors for storing instructions configured for execution by the one or more hardware processors; wherein the one or more hardware processors are configured to receive each raw data sample and further configured to: extract each group of the raw data samples falling within a predefined time window was a raw sub-data sample, wherein the raw sub-data sample comprises the raw foot pressure values, the raw 3-axis accelerometer values, the raw 3-axis gyroscope values, and the associated timestamp t; identify sub-time windows ($m_1, m_2, m_3 \ldots, m_n$) within each of the predefined time window w based on a predefined sub-time window duration d, wherein the raw sub-data sample within each of the sub-time windows comprises the raw 3-axis accelerometer values and the raw 3-axis gyroscope values with the associated timestamp t; determine a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll; obtain a static pressure value for each raw foot pressure value acquired by each piezoelectric sensor of the plurality of piezoelectric sensors, each of the raw foot pressure value being comprised in the raw data samples falling within each predefined time window w, by integrating the associated raw foot pressure values; extract a data sample number having a minimum static pressure value present between each pair of consecutive identified sub-time windows that represent the true stride; calculate drift-free static pressure values ($PC_{ij}$) for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers having the minimum static pressure value; and calculate drift-free plantar pressure parameters in terms of a drift-free Vertical Ground Reaction Force (VGRF) and a 2-dimensional Centre of Pressure (CoP) location for each data sample number falling within each predefined time window w.

In another aspect, there is provided a processor implemented method for calculating drift-free plantar pressure parameters for gait monitoring, the method comprising the steps of: acquiring raw data samples continuously, by one or more hardware processors, using a plurality of piezoelectric sensors and a 6-Degree Of Freedom (DOF) Inertial Measurement Unit (IMU), at a predefined sampling rate, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t; extracting, by the one or more hardware processors, each group of the raw data samples falling within a predefined time window w as a raw sub-data sample, wherein the raw sub-data sample comprises the raw foot pressure values, the raw 3-axis accelerometer values, the raw 3-axis gyroscope values, and the associated timestamp t; identifying, by the one or more hardware processors, sub-time windows ($m_1, m_2, m_3 \ldots, m_n$) within each of the predefined time window w based on a predefined sub-time window duration d, wherein the raw sub-data sample within each of the sub-time windows comprises the raw 3-axis accelerometer values and the raw 3-axis gyroscope values with the associated timestamp t; determining, by the one or more hardware processors, a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll; obtaining, by the one or more hardware processors, a static pressure value for each raw foot pressure value acquired by each piezoelectric sensor of the plurality of piezoelectric sensors, each of the raw foot pressure value being comprised in the raw data samples falling within each predefined time window w, by integrating the associated raw foot pressure values; extracting, by the one or more hardware processors, a data sample number having a minimum static pressure value present between each pair of consecutive identified sub-time windows that represent the true stride; calculating, by the one or more hardware processors, drift-free static pressure values ($PC_{ij}$) for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers; and calculating, by the one or more hardware processors, drift-free plantar pressure parameters in terms of a drift-free Vertical Ground Reaction Force (VGRF) and a 2-dimensional Centre of Pressure (CoP) location for each data sample number falling within each predefined time window w.

In an embodiment of the present disclosure, the step of determining a list of pairs of consecutive identified sub-time windows that represent a true stride comprises: calculating a standard deviation value for each sub-time window ($m_1, m_2, m_3 \ldots, m_n$), based on associated raw 3-axis accelerometer values comprised in the associated sub-time window; identifying a sub-list of the sub-time windows having standard deviation values less than a predefined threshold; calculating a 3-dimensional trajectory for each pair of consecutive identified sub-time windows in the sub-list, based on the associated raw 3-axis accelerometer values and the associated raw 3-axis gyroscope values; determining the trajectory parameters for each pair of the consecutive identified sub-time windows in the sub-list based on an associated 3-dimensional trajectory; and determining the list of pairs of consecutive identified sub-time windows that represent the true stride, wherein the associated determined trajectory parameters satisfies: (i) associated determined trajectory length ranges between predefined upper and lower trajectory length threshold limits; (ii) associated determined trajectory height ranges between predefined upper and lower trajectory height threshold limits; and (iii) associated determined trajectory foot roll is less than a predefined trajectory foot threshold limit.

In an embodiment of the present disclosure, the step of calculating a 3-dimensional trajectory for each pair of consecutive identified sub-time windows comprises: removing gravity from the raw 3-axis accelerometer values using the associated raw 3-axis gyroscope values to obtain linear acceleration values; applying the LiTCEM correction method on the linear acceleration values to obtain corrected acceleration values; integrating the corrected acceleration values over time to determine velocity values; applying the LiTCEM correction method on the determined velocity values to obtain corrected velocity values; and integrating the corrected velocity values to determine displacement values resulting in the 3-dimensional trajectory for the associated pair of consecutive identified sub-time windows.

In an embodiment of the present disclosure, the static pressure value for each raw foot pressure value acquired by each piezoelectric sensor of the plurality of piezoelectric sensors is obtained according to a relation:

$$P_{i,j} = P_{i,(j-1)} + \left(\frac{P_{i,j,r} + P_{i(j-1)r}}{2}\right)\nabla t$$

wherein i represents a piezoelectric sensor number, j represents a data sample number, $\nabla t$ represents a difference in timestamps for data samples 'j−1' and j, $P_{i,j}$ represents the static pressure value for piezoelectric sensor i and data sample number j, $P_{i(j-1)}$ represents the static pressure value for piezoelectric sensor i and previous data sample number 'j−1', $P_{ijr}$, represents the raw foot pressure value for piezoelectric sensor i and data sample number j, and $P_{i(j-1)r}$ represents the raw foot pressure value for piezoelectric sensor i and data sample number 'j−1'.

In an embodiment of the present disclosure, the drift-free Vertical Ground Reaction Force (VGRF) is calculated by adding drift-free static pressure values of the plurality of piezoelectric sensors associated with the data sample number.

In an embodiment of the present disclosure, the drift-free Vertical Ground Reaction Force (VGRF) for each data sample number j falling within each predefined time window w is calculated according to a relation:

$$VGRF_j = \sum_{i=1}^{N} PC_{ij}$$

wherein i represents a piezoelectric sensor number, N represents number of piezoelectric sensors, j represents a data sample number and $PC_{ij}$ represents the drift-free static pressure value for piezoelectric sensor i and data sample number j.

In an embodiment of the present disclosure, the 2-dimensional Centre of Pressure (CoP) location is calculated based on associated drift-free static pressure values, associated drift-free Vertical Ground Reaction Force (VGRF) and locations of associated piezoelectric sensors.

In an embodiment of the present disclosure, the 2-dimensional Centre of Pressure (CoP) location for each data sample number j falling within each predefined time window w is calculated according to a relation:

$$CoP_j = \left(\frac{\sum_{i=1}^{N} PC_{ij} * X_i}{VGRF_j}, \frac{\sum_{i=1}^{N} PC_{ij} * Y_i}{VGRF_j}\right)$$

wherein $(X_i, Y_i)$ represents a 2-dimensional location of the piezoelectric sensor i with respect to plane of a sole of a footwear, j represents the data sample number, $PC_{ij}$ represents the drift-free static pressure value for piezoelectric sensor i and data sample number j, $VGRF_j$ represents the drift-free Vertical Ground Reaction Force (VGRF) for the data sample number j.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1A:
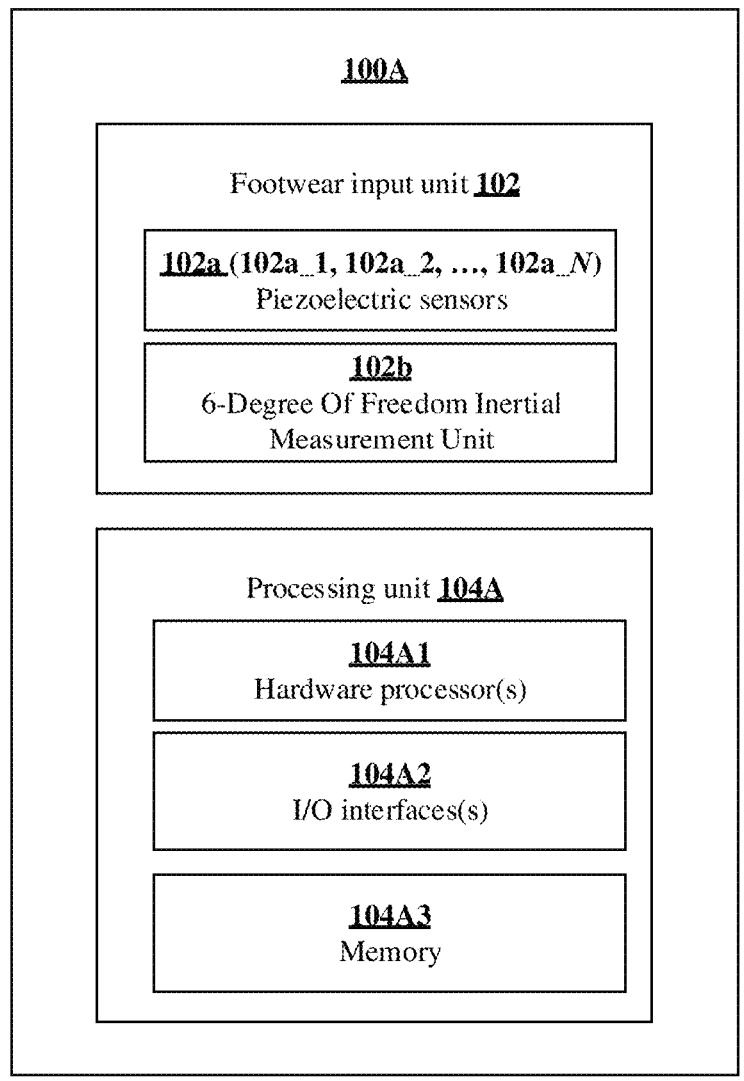
FIG. 1A is a functional block diagram of a wearable apparatus for calculating drift-free plantar pressure parameters for gait monitoring, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Piezoelectric sensors are widely used in many applications as they may easily detect jerks, touches or finger-taps thereby providing an instantaneous and ultra-short duration response. But, the piezoelectric sensors may not directly provide an accurate continuous static pressure measurement especially for long durations for example more than an hour. Hence the provided continuous static pressure measurement for long durations may result in an error which is termed as a drift. In accordance with the present disclosure, the technical problem of the drift that appears when pressure measurements are taken for long durations is addressed by a wearable apparatus and a method for calculating drift-free plantar pressure parameters for gait monitoring which provides a cost-effective solution to calculate drift-free plantar pressure parameters of an individual. Drift-free static pressure data is obtained by numerically integrating the acquired dynamic sensor data from the piezoelectric sensors placed within a sole of a footwear at different positions representing pressure points of a foot of the individual, using a Linear Temporal Cumulated Error Model (LiTCEM) correction mechanism. An Inertial Measurement Unit (IMU sensor) is used for isolating a zero-pressure duration in the acquired dynamic sensor data to prevent the drift, wherein the zero-pressure duration is indicative of the foot of the individual being in air during a stride.

Referring now to the drawings, and more particularly to FIG. 1A through FIG. 5, where similar reference characters denote corresponding features consistently throughout the figures, there are shown preferred embodiments and these embodiments are described in the context of the following exemplary wearable apparatus and the method for calculating drift-free plantar pressure parameters for gait monitoring.

FIG. 1A is a functional block diagram of a wearable apparatus 100A for calculating drift-free plantar pressure parameters for gait monitoring, in accordance with an embodiment of the present disclosure. In an embodiment, the wearable apparatus 100A comprising a footwear input unit 102 and a processing unit 104A. In an embodiment, the footwear input unit 102 comprises a plurality of piezoelectric sensors 102a (102a_1, 102a_2 . . . , 102a_N) and a 6-Degree Of Freedom (DOF) Inertial Measurement Unit (IMU) 102b. In an embodiment, the processing unit 104A comprises one or more processors 104A1, communication interface device(s) or input/output (I/O) interface(s) 104A2, and one or more data storage devices or memory 104A3 operatively coupled to the one or more processors 104A1. In an embodiment, the wearable apparatus 100A may be an in-sole based footwear including a shoe, a sandal and a like. In an embodiment, the plurality of piezoelectric sensors 102a (102a_1, 102a_2 . . . , 102a_N) are off-the shelf piezoelectric sensors generally available in the market.

Figure 1B:
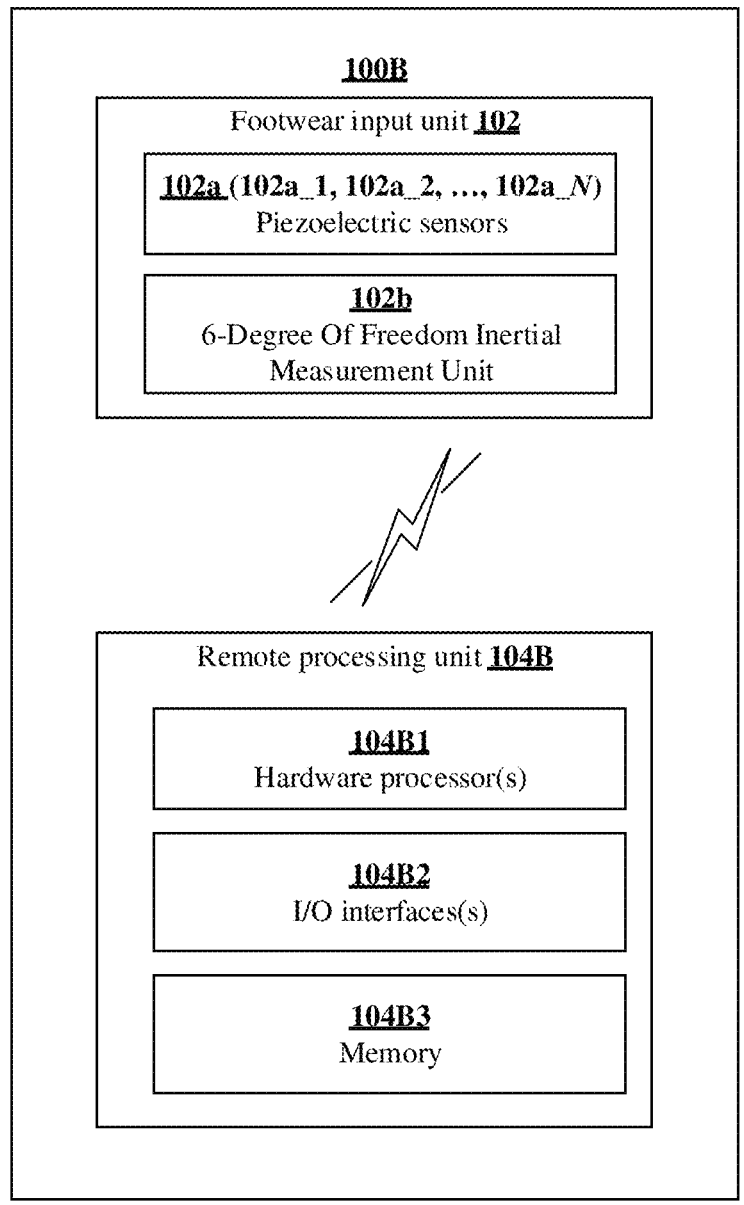
FIG. 1B is a block diagram of a wearable system for calculating drift-free plantar pressure parameters for gait monitoring, in accordance with another embodiment of the present disclosure.

FIG. 1B is a block diagram of a wearable system 100B for calculating drift-free plantar pressure parameters for gait monitoring, in accordance with another embodiment of the present disclosure. In an embodiment, the wearable system 100B comprising a footwear input unit 102 and a remote processing unit 104B. In an embodiment, the footwear input unit 102 comprises a plurality of piezoelectric sensors 102a (102a_1, 102a_2 . . . , 102a_N) and a 6-Degree Of Freedom (DOF) Inertial Measurement Unit (IMU) 102b. In an embodiment, the remote processing unit 104B comprises one or more processors 104B1, communication interface device(s) or input/output (I/O) interface(s) 104B2, and one or more data storage devices or memory 104B3 operatively coupled to the one or more processors 104B1.

In an embodiment, the footwear input unit 102 may be present in an in-sole based footwear including a shoe, a sandal and a like. In an embodiment, the plurality of piezoelectric sensors 102a (102a_1, 102a_2 . . . , 102a_N) are off-the shelf piezoelectric sensors generally available in the market. In an embodiment, the remote processing unit 104B can be implemented in a variety of computing systems, such as laptop computers, notebooks, hand-held devices, workstations, mainframe computers, servers, a network cloud and the like. In an embodiment, the remote processing unit 104B is in communication with the footwear input unit 102 either via a physical connection or with a wireless connection through the communication interface device(s) or input/output (I/O) interface(s) 104B2.

In an embodiment, the one or more processors 104A1 of FIG. 1A and 104B1 of FIG. 1B may be one or more software processing modules or hardware processors and can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) is configured to fetch and execute computer-readable instructions stored in the memory.

The I/O interface device(s) 104A2 of FIG. 1A and 104B2 of FIG. 1B can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

Figure 3:
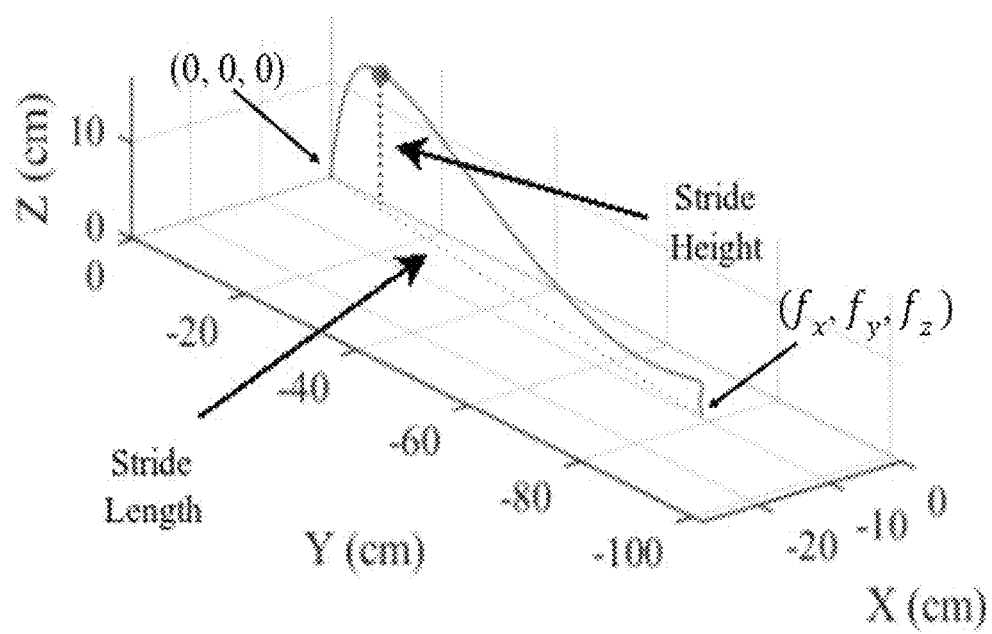
FIG. 3 is a perspective view of a 3-dimensional trajectory of a true stride calculated between a pair of consecutive identified sub-time windows, in accordance with an embodiment of the present disclosure.

The memory 104A3 of FIG. 1A and 104B3 of FIG. 1B may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

In an embodiment, functional aspects and capabilities of components such as the one or more processors (104A1 and 104B1), the communication interface device(s) or input/output (I/O) interface(s) (104A2 and 104B2), and the one or more data storage devices or memory (104A3 and 104B3), of the embodiments illustrated in FIG. 1A and FIG. 1B are the same. But the only difference between the embodiments of FIG. 1A and FIG. 1B is that the processing unit 104A of FIG. 1A is part of the footwear whereas the remote processing unit 104B of FIG. 1B is remote to the footwear, the footwear input unit (102), the processing unit (104A) and the remote processing unit (104B), all being wearable devices.

Figure 2A:
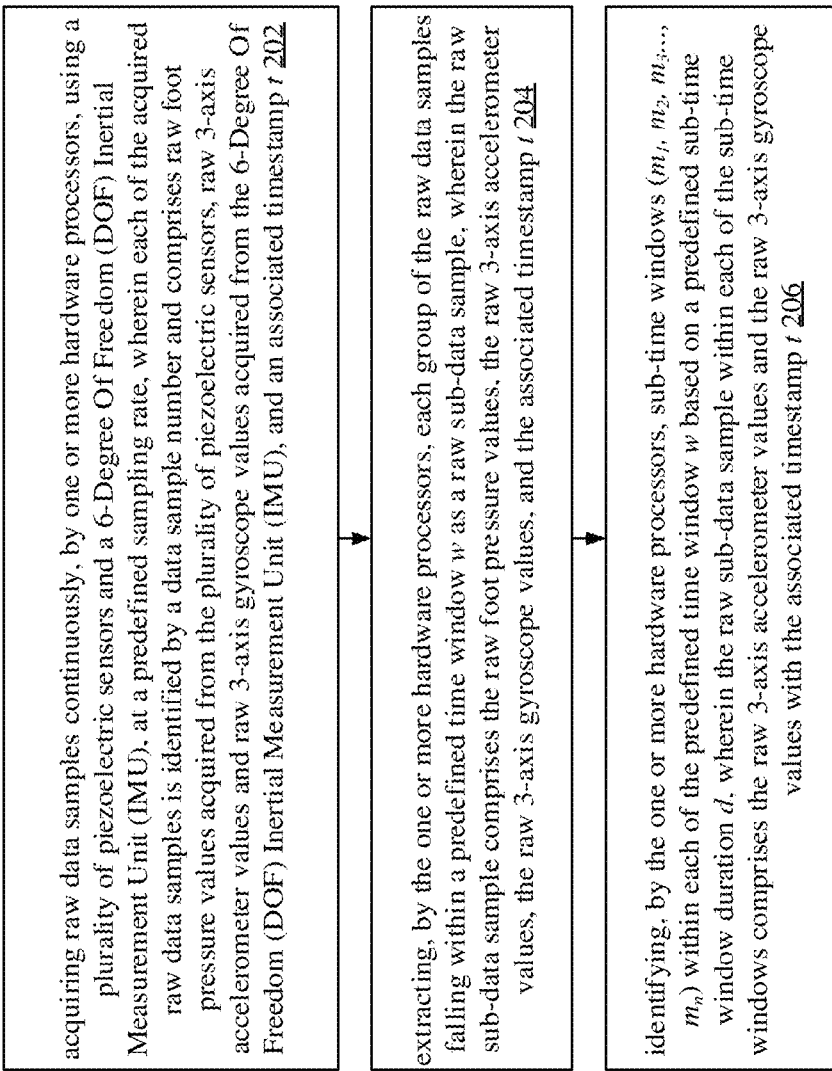
FIG. 2A through FIG. 2C illustrate a flow diagram of a processor implemented method for calculating drift-free plantar pressure parameters for gait monitoring, in accordance with an embodiment of the present disclosure.
Figure 2B:
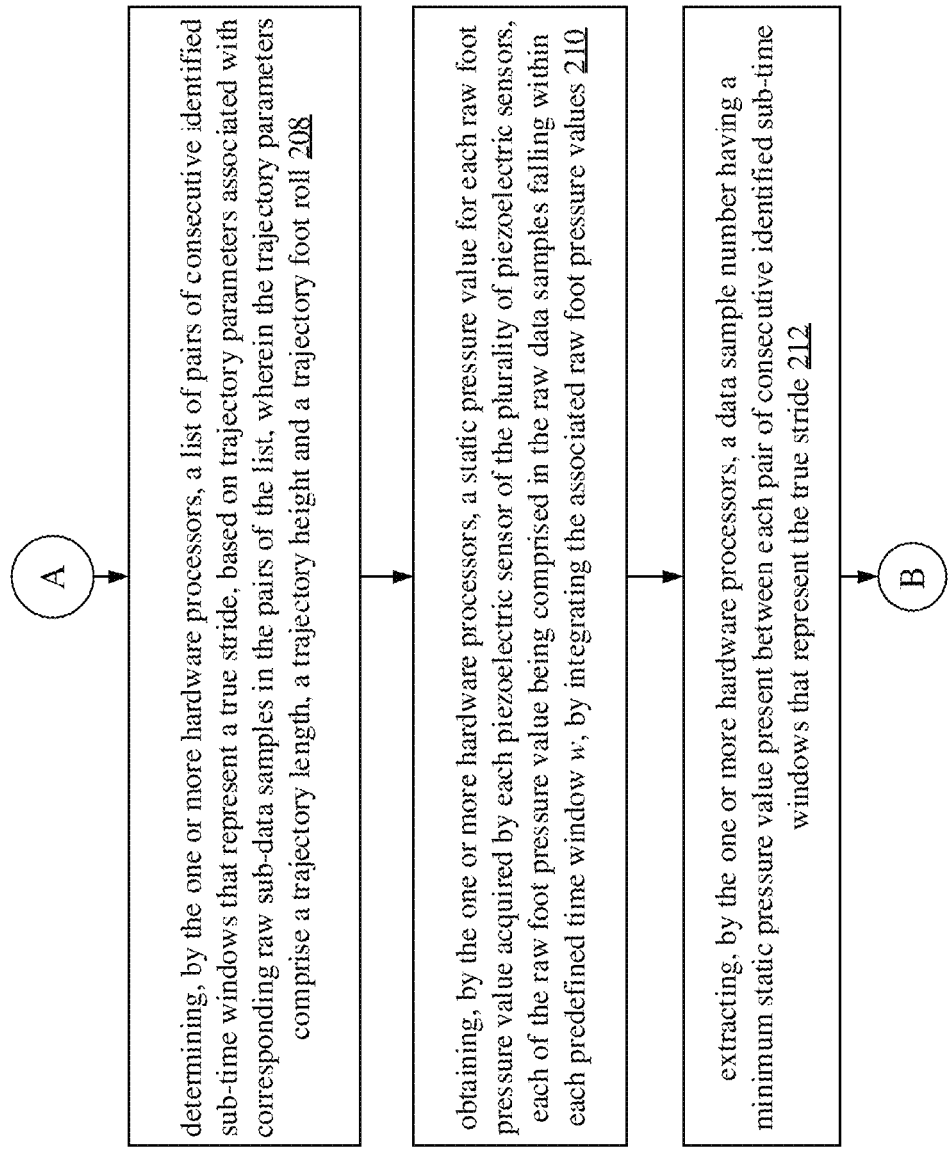
Figure 2C:
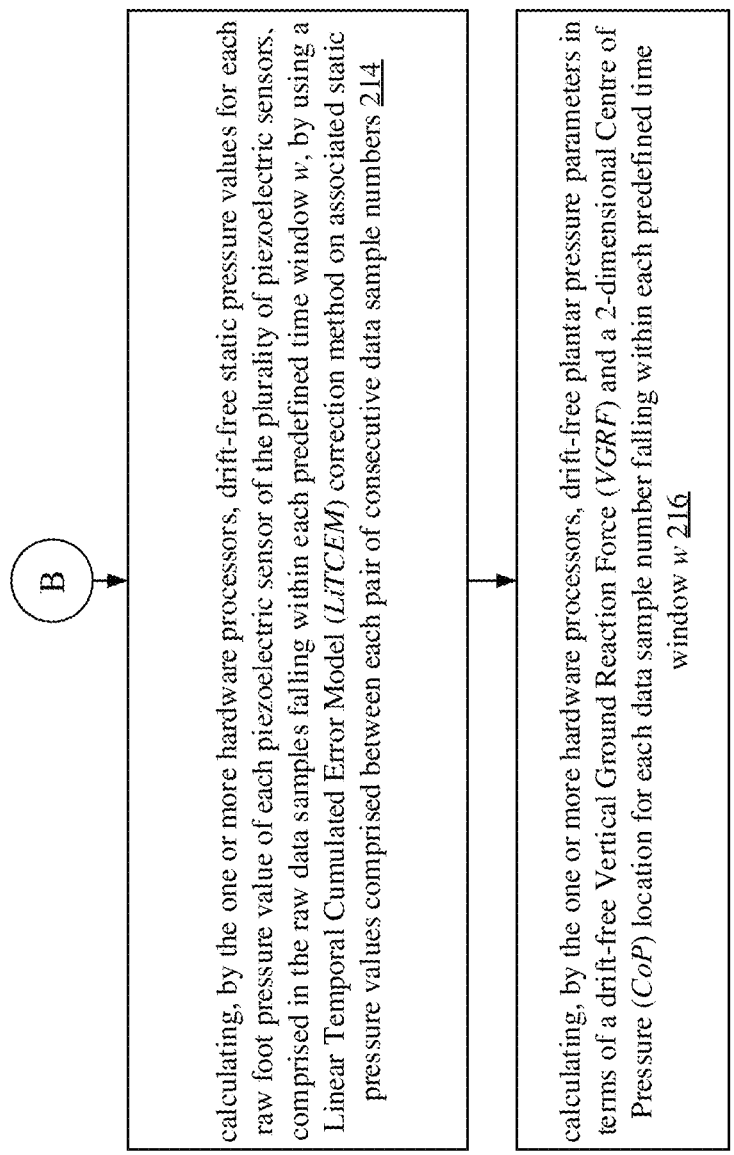

FIG. 2A through FIG. 2C illustrates a flow diagram of a processor implemented method 200 for calculating drift-free plantar pressure parameters for gait monitoring, in accordance with an embodiment of the present disclosure. The steps of the method 200 will now be explained in detail with reference to the wearable apparatus 100A of FIG. 1A and the wearable system 100B of FIG. 1B. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In accordance with an embodiment of the present disclosure, at step 202, raw data samples are acquired continuously at a predefined sampling rate, using a plurality of piezoelectric sensors (102a (102a_1, 102a_2 . . . , 102a_N) of FIG. 1A and FIG. 1B) and a 6-Degree Of Freedom (DOF) Inertial Measurement Unit (IMU) (102b of FIG. 1A and FIG. 1B). In an embodiment five piezoelectric sensors are sufficient to acquire the raw data samples for calculating effective drift-free plantar pressure parameters of the individual. In an embodiment, the plurality of piezoelectric sensors (102a (102a_1, 102a_2 . . . , 102a_N) of FIG. 1A and FIG. 1B) are placed within a sole of a footwear at different positions representing pressure points of a foot of the individual. In an embodiment, the five typical pressure points are interphalangeal joint, metatarsophalangeal joint, heel, lateral calcaneus and distal Metatarsophalangeal joint.

In an embodiment, the 6-Degree Of Freedom (DOF) Inertial Measurement Unit (IMU) (102*b* of FIG. 1A and FIG. 1B) is placed at bottom of the footwear representing mid foot area of the individual. In an embodiment, raw data samples are acquired continuously at the predefined sampling rate even when the footwear is not being worn by the individual. In an embodiment, the predefined sampling rate may be 100 Hertz (100 samples per second). In an embodiment, the footwear may be an in-sole based footwear including a shoe, a sandal and the like.

Each of the acquired raw data samples is identified by a data sample number. Each of the acquired raw data samples comprises raw foot pressure values acquired from the plurality of piezoelectric sensors (102*a* (102*a*_1, 102*a*_2 . . . , 102*a*_N) of FIG. 1A and FIG. 1B), raw 3-axis accelerometer values and raw 3-axis gyroscope values acquired from the 6-Degree Of Freedom (DOF) Inertial Measurement Unit (IMU) (102*b* of FIG. 1A and FIG. 1B), and an associated timestamp t. The raw foot pressure values represent electric voltage values that are generated due to change in mechanical stress or forces applied along a vertical plane, while walking, standing, moving or running by the individual. Similarly, the raw 3-axis accelerometer values represent acceleration values along X-axis, Y-axis and Z-axis that are generated due to the acceleration forces while walking, standing, moving or running by the individual. The acceleration values comprise linear acceleration values and acceleration components due to a gravity. The raw 3-axis gyroscope values represent angular speed values along X-axis, Y-axis and Z-axis defining an orientation of the individual while walking, standing, moving or running.

In an embodiment, each of the acquired raw data samples may be represented in a following format:

$$S_j = (t_j, (P_{1jr}, P_{2jr}, P_{3jr}, \ldots P_{Njr}), (A_{Xjr}, A_{Yjr}, A_{Zjr}), (G_{Xjr}, G_{Yjr}, G_{Zjr}))$$

wherein j represents a data sample number, $S_j$ represents a raw data sample for the data sample number j, $(P_{1jr}, P_{2jr}, P_{3jr}, \ldots P_{Njr})$ represents raw foot pressure values of each piezoelectric sensor of the N piezoelectric sensors (102*a* (102*a*_1, 102*a*_2 . . . , 102*a*_N) of FIG. 1A and FIG. 1B) for the data sample number j, $(A_{Xjr}, A_{Yjr}, A_{Zjr})$ represents the raw 3-axis accelerometer values along X-axis, Y-axis and Z-axis, $(G_{Xjr}, G_{Yjr}, G_{Zjr})$ represents the raw 3-axis gyroscope values along X-axis, Y-axis and Z-axis, r denotes that each value in the data sample is raw and $t_j$ represents a timestamp for the data sample number j.

In accordance with an embodiment of the present disclosure, the one or more hardware processors 104A1 of FIG. 1A and 104B1 of FIG. 1B are configured to extract, at step 204, each group of the raw data samples falling within a predefined time window w as a raw sub-data sample. In an embodiment, the raw sub-data sample comprises the raw foot pressure values, the raw 3-axis accelerometer values, the raw 3-axis gyroscope values, and the associated timestamp t. In an embodiment, the predefined time window w may be 160 seconds. In an embodiment, each raw sub-data sample comprises 16,000 number of samples when the predefined time window w is 160 seconds and the predefined sampling rate is 100 Hertz.

In an embodiment, the one or more hardware processors 104A1 of FIG. 1A and 104B1 of FIG. 1B are configured to receive each raw data sample acquired using the plurality of piezoelectric sensors (102*a* (102*a*_1, 102*a*_2 . . . , 102*a*_N) of FIG. 1A and FIG. 1B) and the 6-Degree Of Freedom (DOF) Inertial Measurement Unit (IMU) (102*b* of FIG. 1A and FIG. 1B), before extracting each group of the raw data samples falling within a predefined time window was a raw sub-data sample.

In accordance with an embodiment of the present disclosure, the one or more hardware processors 104A1 of FIG. 1A and 104B1 of FIG. 1B are configured to identify, at step 206, sub-time windows $(m_1, m_2, m_3 \ldots, m_n)$ within each of the predefined time window w, based on a predefined sub-time window duration d. In an embodiment, the raw sub-data sample within each of the sub-time windows comprises the raw 3-axis accelerometer values and the raw 3-axis gyroscope values with the associated timestamp t.

In an embodiment, the predefined sub-time window duration d may be 0.5 seconds. Then, each of the sub-time windows comprises 50 number of raw sub-data samples, when the predefined time window w is 160 seconds, the predefined sampling rate is 100 Hertz and the predefined sub-time window duration d is 0.5 seconds. Accordingly each of the predefined time window w comprises 320 number of sub-time windows $(m_1, m_2, m_3 \ldots, m_n)$.

In accordance with an embodiment of the present disclosure, the one or more hardware processors 104A1 of FIG. 1A and 104B1 of FIG. 1B are configured to determine, at step 208, a list of pairs of consecutive identified sub-time windows that represent a true stride, based on trajectory parameters associated with corresponding raw sub-data samples in the pairs of the list. The trajectory parameters comprise a trajectory length, a trajectory height and a trajectory foot roll.

In an embodiment, a standard deviation value for each sub-time window $(m_1, m_2, m_3 \ldots, m_n)$, is calculated based on associated raw 3-axis accelerometer values comprised in the associated sub-time window. A sub-list of the sub-time windows whose standard deviation values less than a predefined threshold is identified. A 3-dimensional trajectory for each pair of consecutive identified sub-time windows in the sub-list is calculated, based on the associated raw 3-axis accelerometer values and the associated raw 3-axis gyroscope values. The trajectory parameters for each pair of the consecutive identified sub-time windows in the sub-list are determined based on an associated 3-dimensional trajectory. The list of pairs of consecutive identified sub-time windows that represent the true stride are determined based on the associated determined trajectory parameters satisfying: (i) associated determined trajectory length ranges between predefined upper and lower trajectory length threshold limits; (ii) associated determined trajectory height ranges between predefined upper and lower trajectory height threshold limits; and (iii) associated determined trajectory foot roll is less than a predefined trajectory foot threshold limit.

In an embodiment, the 3-dimensional trajectory for each pair of consecutive identified sub-time windows is determined by removing gravity from the raw 3-axis accelerometer values using the associated raw 3-axis gyroscope values to obtain linear acceleration values.

The raw 3-axis accelerometer values may vary from actual accelerometer values due to various factors including internal vibrations, manufacturing bias, temperature changes, cross axes interference etc. This trend of error defining the difference between the actual accelerometer values and the raw 3-axis accelerometer values, is termed as drift. When performing a numerical integration to determine the velocity values, the drift goes up and net drift rate may be intensified in subsequent calculations.

In an embodiment, a Linear Temporal Cumulated Error Model (LiTCEM) correction method is applied on the linear acceleration values to obtain corrected acceleration values for resolving the drift. The LiTCEM correction method is a form of zero correction mechanism which works on a single data section at a time. The single data section is chosen in such a way that the starting and ending values in the single data section should be zero. The LiTCEM correction method is performed on the single data section comprising a plurality of values as follows: (i) a first value in the single data section is subtracted from the plurality of values present in the single data section; (ii) a last value present in the resultant single data section represents a cumulated error which is then subtracted from plurality of values present in the resultant single data section linearly with time to obtain error-free single data section comprising corrected plurality of values.

In an embodiment, the first linear acceleration value is subtracted from the linear acceleration values of the data section to obtain the revised data section with the linear acceleration values, then the last linear acceleration value present in the revised data section is subtracted from the linear acceleration values of the revised data section, linearly with time to obtain corrected linear acceleration values. The corrected linear acceleration values are numerically integrated over time to determine velocity values. In an embodiment, the data section of the linear acceleration values represents the linear acceleration values present in associated pair of consecutive identified sub-time windows.

Again, the LiTCEM correction method is applied on the determined velocity values to obtain corrected velocity values. The first velocity value is subtracted from the determined velocity values of the data section to obtain the revised data section with the velocity values, then the last velocity value present in the revised data section is subtracted from the velocity values of the revised data section, linearly with time to obtain corrected velocity values. The obtained corrected velocity values are integrated over time to calculate the 3-dimensional trajectory for the associated pair of consecutive identified sub-time windows.

In an embodiment, the trajectory length is determined as a Euclidean distance between a start point and an end point of the associated 3-dimensional trajectory. The trajectory height is defined as a maximum distance between the ground and the foot during the stride. The trajectory foot roll represents an angle of rotation of the foot during traversing the trajectory about a vertical direction (direction opposite to gravity). In an embodiment, the angle of rotation of the foot is determined by numerically integrating the raw gyroscope values representing the angular speed values along the vertical direction using trapezoidal integration.

In accordance with an embodiment of the present disclosure, the one or more hardware processors 104A1 of FIG. 1A and 104B1 of FIG. 1B are configured to obtain, at step 210, a static pressure value for each raw foot pressure value acquired by each piezoelectric sensor of the plurality of piezoelectric sensors (102a (102a_1, 102a_2 ... , 102a_N) of FIG. 1A and FIG. 1B), by integrating the associated raw foot pressure values over time. Each of the raw foot pressure value being comprised in the raw data samples falling within each predefined time window w. The static pressure value for each raw foot pressure value may comprises the drift due to the integration of the associated raw foot pressure values over time, which has to be removed.

In an embodiment, the static pressure value for each raw foot pressure value acquired by each piezoelectric sensor of the plurality of piezoelectric sensors (102a (102a_1, 102a_2 ... , 102a_N) of FIG. 1A and FIG. 1B), is obtained according to a relation:

$$P_{i,j} = P_{i,(j-1)} + \left(\frac{P_{ijr} + P_{i(j-1)r}}{2}\right)\nabla t$$

wherein i represents a piezoelectric sensor number, j represents a data sample number, $\nabla t$ represents a difference in timestamps for data samples 'j-1' and j, $P_{ijr}$ represents the static pressure value for piezoelectric sensor i and data sample number j, $P_{i,(j-1)}$ represents the static pressure value for piezoelectric sensor i and previous data sample number 'j-1', $P_{ijr}$ represents the raw foot pressure value for piezoelectric sensor i and data sample number j, and $P_{i(j-1)r}$ represents the raw foot pressure value for piezoelectric sensor i and data sample number 'j-1'.

In accordance with an embodiment of the present disclosure, the one or more hardware processors 104A1 of FIG. 1A and 104B1 of FIG. 1B are configured to extract, at step 212, a data sample number having a minimum static pressure value present between each pair of consecutive identified sub-time windows that represent the true stride. The minimum static pressure value present between each pair of consecutive identified sub-time windows that represent the true stride is supposed to be zero representing a zero pressure duration, when the foot of the individual is in the air. But due to the drift resulted while obtaining the static pressure value by integrating the associated raw foot pressure values, the zero pressure duration is not observed, which has to be corrected.

In accordance with an embodiment of the present disclosure, the one or more hardware processors 104A1 of FIG. 1A and 104B1 of FIG. 1B are configured to calculate, at step 214, drift-free static pressure values ($PC_{ij}$) for each raw foot pressure value of each piezoelectric sensor of the plurality of piezoelectric sensors (102a (102a_1, 102a_2 ... , 102a_N) of FIG. 1A and FIG. 1B), comprised in the raw data samples falling within each predefined time window w, using the Linear Temporal Cumulated Error Model (LiTCEM) correction method. In an embodiment, the LiTCEM correction method is applied on associated static pressure values comprised between each pair of consecutive data sample numbers having the minimum static pressure value, to calculate the drift-free static pressure values ($PC_{ij}$).

According to the LiTCEM correction method, the first static pressure value is subtracted from the obtained static pressure values of the data section to obtain the revised data section with the static pressure values, then the last static pressure value present in the revised data section is subtracted from the static pressure values of the revised data section, linearly with time to obtain the drift-free static pressure values ($PC_{ij}$).

In accordance with an embodiment of the present disclosure, the one or more hardware processors 104A1 of FIG. 1A and 104B1 of FIG. 1B are configured to calculate, at step 216, drift-free plantar pressure parameters in terms of a drift-free Vertical Ground Reaction Force (VGRF) and a 2-dimensional Centre of Pressure (CoP) location for each data sample number falling within each predefined time window w. In an embodiment, the drift-free plantar pressure parameters are measured for each raw data sample along with the associated timestamp t.

In an embodiment, the drift-free Vertical Ground Reaction Force (VGRF) is calculated by adding drift-free static pressure values of the plurality of piezoelectric sensors (102a (102a_1, 102a_2 ... , 102a_N) of FIG. 1A and FIG. 1B) associated with the data sample number.

In an embodiment, the drift-free Vertical Ground Reaction Force (VGRF) for each data sample number j falling within each predefined time window w is calculated according to a relation:

$$VGRF_j = \sum_{i=1}^{N} PC_{ij}$$

wherein i represents a piezoelectric sensor number, N represents number of piezoelectric sensors, j represents a data sample number and $PC_{ij}$ represents the drift-free static pressure value for piezoelectric sensor i and data sample number j.

In an embodiment, the 2-dimensional Centre of Pressure (CoP) location is calculated based on associated drift-free static pressure values, associated drift-free Vertical Ground Reaction Force (VGRF) and locations of associated piezoelectric sensors. In an embodiment, the locations of associated piezoelectric sensors are the physical locations where the associated piezoelectric sensors placed in the sole of the footwear, representing pressure points of the foot including interphalangeal joint, metatarsophalangeal joint, heel, lateral calcaneus and distal Metatarsophalangeal joint.

In an embodiment, the 2-dimensional Centre of Pressure (CoP) location for each data sample number j falling within each predefined time window w is calculated according to a relation:

$$CoP_j = \left( \frac{\sum_{i=1}^{N} PC_{ij} * X_i}{VGRF_j}, \frac{\sum_{i=1}^{N} PC_{ij} * Y_i}{VGRF_j} \right)$$

wherein $(X_i, Y_i)$ represents a 2-dimensional location of the piezoelectric sensor i with respect to plane of a sole of a footwear, j represents the data sample number, $PC_{ij}$ represents the drift-free static pressure value for piezoelectric sensor i and data sample number j, $VGRF_j$ represents the drift-free Vertical Ground Reaction Force (VGRF) for the data sample number j.

FIG. 3 is a perspective view of a 3-dimensional trajectory of a true stride calculated between a pair of consecutive identified sub-time windows, in accordance with an embodiment of the present disclosure. The trajectory parameters comprising the trajectory length, the trajectory height and the trajectory foot roll are determined based on the 3-dimensional trajectory for the associated pair of consecutive identified sub-time windows. In an embodiment, the trajectory length is determined as the Euclidean distance between the start point and the end point of the associated 3-dimensional trajectory. If the start point is (0, 0, 0) and the end point is $(f_x, f_y, f_z)$ as represent in FIG. 3, then the trajectory length is determined according to a relation:

$$\text{Trajectory Length} = \sqrt{(f_x^2 + f_y^2 + f_z^2)}$$

In an embodiment, let coordinates of the 3-dimensional trajectory be represented as $(C_1, C_2, C_3, \ldots, C_n)$ where $C_1$ is the start point (0, 0, 0) and $C_n$ is the end point is $(f_x, f_y, f_z)$, let a vector from the start point (0, 0, 0) to the end point is $(f_x, f_y, f_z)$ be represented as L, and let a distance between the coordinate C, (where i=1, 2, 3, ... n)) and the vector L be represented as $r_i$, then the trajectory height is determined as the distance of the farthest coordinate of the 3-dimensional trajectory from the vector L and according to a relation:

$$\text{Trajectory Height} = \max(r_i) \text{ for all } 1 \le i \le n$$

Figure 4:
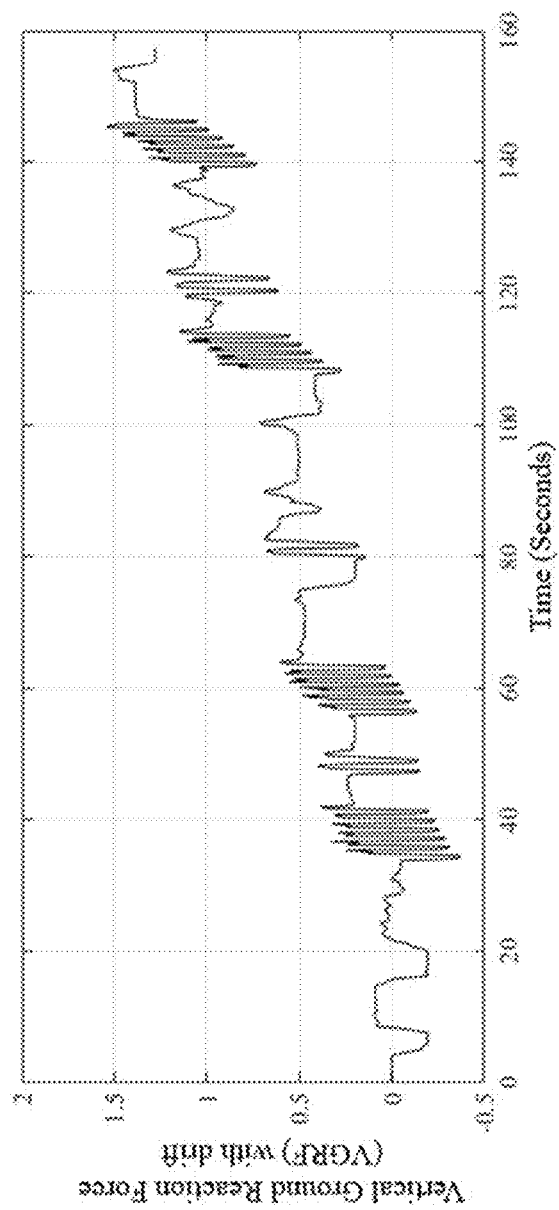
FIG. 4 is a graph showing vertical ground reaction force calculated from static pressure values having a drift for data samples falling within a time window of 160 seconds, in accordance with an embodiment of the present disclosure.
Figure 5:
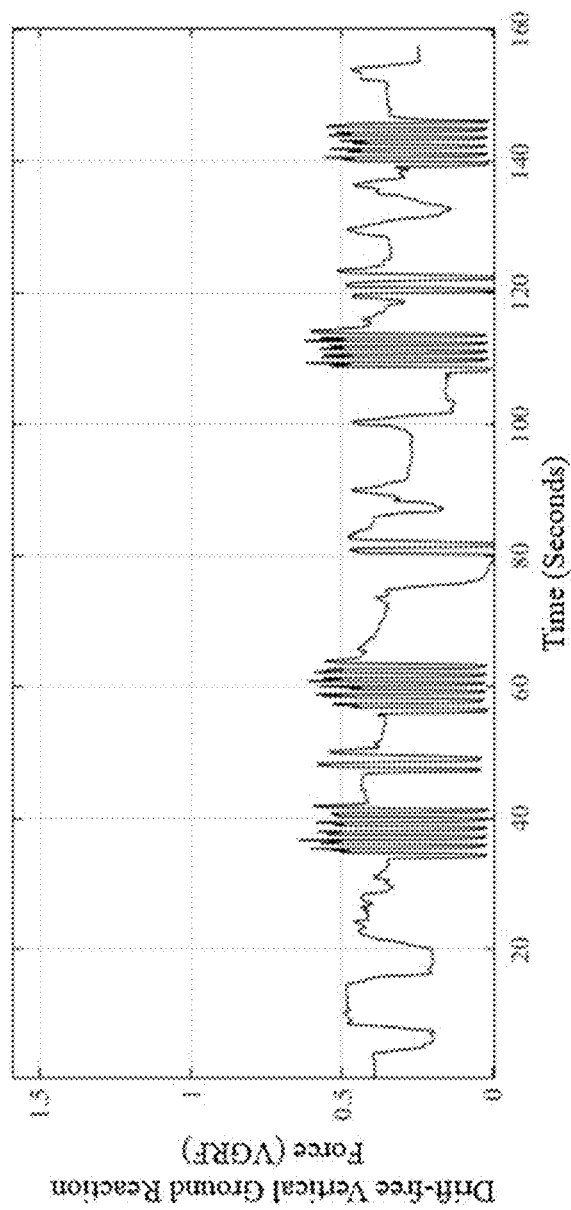
FIG. 5 is a graph showing drift-free vertical ground reaction force calculated from drift-free static pressure values for data samples falling within a time window of 160 seconds, in accordance with an embodiment of the present disclosure.

FIG. 4 is a graph showing vertical ground reaction force calculated from static pressure values having a drift for data samples falling within a time window of 160 seconds, in accordance with an embodiment of the present disclosure. FIG. 5 is a graph showing drift-free vertical ground reaction force calculated from drift-free static pressure values for data samples falling within a time window of 160 seconds, in accordance with an embodiment of the present disclosure. In FIG. 5, the zero-pressure duration is present to show the drift-free static pressure values as zero which is indicative of the foot of the individual being in the air during the stride, resulting in vertical ground reaction force (VGRF) zero, but due to the drift in static pressure values, the vertical ground reaction force (VGRF) is instead non zero and gradually increasing as depicting in FIG. 4 which is inaccurate and normally not possible.

In an embodiment, the drift-free plantar pressure parameters are stored in the memory 104A3 of FIG. 1A and 104B3 of FIG. 1B. The stored drift-free plantar pressure parameters are helpful for analyzing walking patterns which further helps in monitoring gait of the individual. The gait monitoring includes evaluating Parkinsonian gait, mobility and walking disorders of the individual. Also, the drift-free plantar pressure parameters are helpful in evaluating running performance of an athlete. The individual may be a healthy person, a person with walking disorders or an athlete. The wearable apparatus 100A and the wearable system 100B of the present disclosure calculates the drift-free plantar pressure parameters of living beings, in general for gait monitoring, wherein the living beings may include animals.

The remote processing unit 104B of FIG. 1B may be a desktop or a portable electronic device including a mobile phone, a smart phone, hand-held device or a Personal Digital Assistant (PDA). Hence the drift-free plantar pressure parameters may be evaluated on such portable or desktop electronic devices and walking patterns may be analyzed dynamically.

Thus, in accordance with the present disclosure, drift-free plantar pressure parameters are calculated using the drift-free static pressure data which is obtained by numerically integrating the acquired dynamic sensor data from the piezoelectric sensors, using the LiTCEM correction mechanism. The 6-DOF Inertial Measurement Unit (IMU sensor) helps in isolating the zero-pressure duration which is indicative of foot of the individual being in the air during the stride, while obtaining drift-free static pressure data. The disclosed wearable apparatus is very less expensive compare to the existing wearable devices, as off-the shelf piezoelectric sensors are used which are generally available in the market. The disclosed wearable apparatus and the wearable system calculate the drift-free plantar pressure parameters for long durations and hence is very helpful in monitoring the walking patterns of the individual for long durations effectively. Apart from the drift-free plantar pressure parameters, the disclosed wearable apparatus and the wearable system also calculate the drift-free kinematic parameters such as the trajectory length, the trajectory height and the trajectory foot roll which are helpful in analysing walking speed, angular velocity and so on of the individual. The disclosed wearable apparatus is easily wearable and flexible.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by the one or more processors described herein after may be implemented in one or more modules.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims (when included in the specification), the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A wearable apparatus for calculating drift-free plantar pressure parameters for gait monitoring of an individual, the apparatus comprising:
a footwear input unit comprising:
a plurality of piezoelectric sensors placed within a sole of a footwear at different positions representing pressure points of a foot and a 6-Degree Of Freedom (DOF) Inertial Measurement Unit (IMU) placed at bottom of the footwear representing a mid-foot area, to acquire raw data samples continuously at a predefined sampling rate pertaining to an individual, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t; and
a processing unit comprising one or more internal data storage devices operatively coupled to one or more hardware processors for storing instructions configured for execution by the one or more hardware processors; wherein the one or more hardware processors are configured to receive each raw data sample and further configured to:
extract each group of the raw data samples falling within a predefined time window 'w' as a raw sub-data sample pertaining to the individual, wherein the raw sub-data sample comprises the raw foot pressure values, the raw 3-axis accelerometer values, the raw 3-axis gyroscope values, and the associated timestamp t;
identify sub-time windows $(m_1, m_2, m_3 \ldots, m_n)$ within each of the predefined time window w based on a predefined sub-time window duration d, wherein the raw sub-data sample within each of the sub-time windows comprises the raw 3-axis accelerometer values and the raw 3-axis gyroscope values with the associated timestamp t;
determine a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll;
obtain a static pressure value for each raw foot pressure value acquired by each piezoelectric sensor of the plurality of piezoelectric sensors, each of the raw foot pressure value being comprised in the raw data samples falling within each predefined time window w, by integrating associated raw foot pressure values;
extract a data sample number having a minimum static pressure value present between each pair of consecutive identified sub-time windows that represent the true stride;
calculate drift-free static pressure values $(PC_{ij})$ for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers having the minimum static pressure value; and calculate drift-free plantar pressure parameters in terms of a drift-free Vertical Ground Reaction Force (VGRF) and a 2-dimensional Centre of Pressure (CoP) location for each data sample number falling within each predefined time window w, and using the drift-free plantar pressure parameters to analyze walking pattern of the individual for gait monitoring.

2. The wearable apparatus of claim 1, wherein the one or more hardware processors are further configured to:

calculate a standard deviation value for each sub-time window $(m_1, m_2, m_3, \ldots, m_n)$, based on associated raw 3-axis accelerometer values comprised in associated sub-time window;

identify a sub-list of the sub-time windows having standard deviation values less than a predefined threshold;

calculate a 3-dimensional trajectory for each pair of consecutive identified sub-time windows in the sub-list, based on the associated raw 3-axis accelerometer values and the associated raw 3-axis gyroscope values;

determine the trajectory parameters for each pair of the consecutive identified sub-time windows in the sub-list based on an associated 3-dimensional trajectory; and determine the list of pairs of consecutive identified sub-time windows that represent the true stride, wherein associated determined trajectory parameters satisfies:

(i) associated determined trajectory length ranges between predefined upper and lower trajectory length threshold limits;

(ii) associated determined trajectory height ranges between predefined upper and lower trajectory height threshold limits; and (iii) associated determined trajectory foot roll is less than a predefined trajectory foot threshold limit.

3. The wearable apparatus of claim 2, wherein the one or more hardware processors are further configured to:

remove gravity from the raw 3-axis accelerometer values using the associated raw 3-axis gyroscope values to obtain linear acceleration values;

apply the LiTCEM correction method on the linear acceleration values to obtain corrected acceleration values;

integrate the corrected acceleration values over time to determine velocity values;

apply the LiTCEM correction method on the determined velocity values to obtain corrected velocity values; and integrate the corrected velocity values to determine displacement values resulting in a 3-dimensional trajectory for associated pair of consecutive identified sub-time windows.

4. The wearable apparatus of claim 1, wherein the one or more hardware processors are further configured to calculate the drift-free Vertical Ground Reaction Force (VGRF), by adding drift-free static pressure values of the plurality of piezoelectric sensors associated with the data sample number.

5. The wearable apparatus of claim 1, wherein the one or more hardware processors are further configured to calculate the 2-dimensional Centre of Pressure (CoP) location, based on associated drift-free static pressure values, associated drift-free Vertical Ground Reaction Force (VGRF) and locations of associated piezoelectric sensors.

6. The wearable apparatus of claim 1, wherein the one or more hardware processors are configured to use the trajectory parameters for analyzing at least one of walking speed and angular velocity of the individual.

7. A wearable system for calculating drift-free plantar pressure parameters for gait monitoring of an individual, the system comprising:

a footwear input unit comprising:

a plurality of piezoelectric sensors placed within a sole of a footwear at different positions representing pressure points of a foot and a 6-Degree Of Freedom (DOF) Inertial Measurement Unit (IMU) placed at bottom of the footwear representing a mid-foot area, to acquire raw data samples continuously at a predefined sampling rate pertaining to an individual, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t; and a remote processing unit comprising one or more internal data storage devices operatively coupled to one or more hardware processors for storing instructions configured for execution by the one or more hardware processors; wherein the one or more hardware processors are configured to receive each raw data sample and further configured to:

extract each group of the raw data samples falling within a predefined time window 'w' as a raw sub-data sample pertaining to the individual, wherein the raw sub-data sample comprises the raw foot pressure values, the raw 3-axis accelerometer values, the raw 3-axis gyroscope values, and the associated timestamp t;

identify sub-time windows $(m_1, m_2, m_3 \ldots, m_n)$ within each of the predefined time window w based on a predefined sub-time window duration d, wherein the raw sub-data sample within each of the sub-time windows comprises the raw 3-axis accelerometer values and the raw 3-axis gyroscope values with the associated timestamp t;

determine a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll;

obtain a static pressure value for each raw foot pressure value acquired by each piezoelectric sensor of the plurality of piezoelectric sensors, each of the raw foot pressure value being comprised in the raw data samples falling within each predefined time window w, by integrating the associated raw foot pressure values;

extract a data sample number having a minimum static pressure value present between each pair of consecutive identified sub-time windows that represent the true stride;

calculate drift-free static pressure values $(PC_{ij})$ for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers having the minimum static pressure value; and calculate drift-free plantar pressure parameters in terms of a drift-free Vertical Ground Reaction Force (VGRF)

and a 2-dimensional Centre of Pressure (CoP) location for each data sample number falling within each predefined time window w, and using the drift-free plantar pressure parameters to analyze walking pattern of the individual for gait monitoring.

8. The wearable system of claim 7, wherein the one or more hardware processors are further configured to:

calculate a standard deviation value for each sub-time window ($m_1, m_2, m_3, \ldots, m_n$), based on associated raw 3-axis accelerometer values comprised in the associated sub-time window;

identify a sub-list of the sub-time windows having standard deviation values less than a predefined threshold;

calculate a 3-dimensional trajectory for each pair of consecutive identified sub-time windows in the sub-list, based on the associated raw 3-axis accelerometer values and associated raw 3-axis gyroscope values;

determine the trajectory parameters for each pair of the consecutive identified sub-time windows in the sub-list based on an associated 3-dimensional trajectory; and determine the list of pairs of consecutive identified sub-time windows that represent the true stride, wherein associated determined trajectory parameters satisfies:

(i) associated determined trajectory length ranges between predefined upper and lower trajectory length threshold limits;

(ii) associated determined trajectory height ranges between predefined upper and lower trajectory height threshold limits; and (iii) associated determined trajectory foot roll is less than a predefined trajectory foot threshold limit.

9. The wearable system of claim 8, wherein the one or more hardware processors are further configured to:

remove gravity from the raw 3-axis accelerometer values using the associated raw 3-axis gyroscope values to obtain linear acceleration values;

apply the LiTCEM correction method on the linear acceleration values to obtain corrected acceleration values;

integrate the corrected acceleration values over time to determine velocity values;

apply the LiTCEM correction method on the determined velocity values to obtain corrected velocity values; and integrate the corrected velocity values to determine displacement values resulting in a 3-dimensional trajectory for the associated pair of consecutive identified sub-time windows.

10. The wearable system of claim 7, wherein the one or more hardware processors are further configured to calculate the drift-free Vertical Ground Reaction Force (VGRF), by adding drift-free static pressure values of the plurality of piezoelectric sensors associated with the data sample number.

11. The wearable system of claim 7, wherein the one or more hardware processors are further configured to calculate the 2-dimensional Centre of Pressure (CoP) location, based on associated drift-free static pressure values, associated drift-free Vertical Ground Reaction Force (VGRF) and locations of associated piezoelectric sensors.

12. A processor implemented method for calculating drift-free plantar pressure parameters for gait monitoring of an individual, the method comprising the steps of:

acquiring raw data samples continuously, by one or more hardware processors, using a plurality of piezoelectric sensors and a 6-Degree Of Freedom (DOF) Inertial Measurement Unit (IMU), at a predefined sampling rate pertaining to an individual, wherein each of the acquired raw data samples is identified by a data sample number and comprises raw foot pressure values acquired from the plurality of piezoelectric sensors, raw 3-axis accelerometer values and raw 3-axis gyroscope values acquired from the 6-Degree Of Freedom (DOF) Inertial Measurement Unit (IMU), and an associated timestamp t;

extracting, by the one or more hardware processors, each group of the raw data samples falling within a predefined time window w as a raw sub-data sample pertaining to an individual, wherein the raw sub-data sample comprises the raw foot pressure values, the raw 3-axis accelerometer values, the raw 3-axis gyroscope values, and the associated timestamp t;

identifying, by the one or more hardware processors, sub-time windows ($m_1, m_2, m_3, \ldots, m_n$) within each of the predefined time window w based on a predefined sub-time window duration d, wherein the raw sub-data sample within each of the sub-time windows comprises the raw 3-axis accelerometer values and the raw 3-axis gyroscope values with the associated timestamp t;

determining, by the one or more hardware processors, a list of pairs of consecutive identified sub-time windows that represent a true stride, based on trajectory parameters associated with corresponding raw sub-data samples in the pairs of the list, wherein the trajectory parameters comprise a trajectory length, a trajectory height and a trajectory foot roll;

obtaining, by the one or more hardware processors, a static pressure value for each raw foot pressure value acquired by each piezoelectric sensor of the plurality of piezoelectric sensors, each of the raw foot pressure value being comprised in the raw data samples falling within each predefined time window w, by integrating associated raw foot pressure values;

extracting, by the one or more hardware processors, a data sample number having a minimum static pressure value present between each pair of consecutive identified sub-time windows that represent the true stride;

calculating, by the one or more hardware processors, drift-free static pressure values ($PC_{ij}$) for each raw foot pressure value of each piezoelectric sensor of the plurality of piezoelectric sensors, comprised in the raw data samples falling within each predefined time window w, by using a Linear Temporal Cumulated Error Model (LiTCEM) correction method on associated static pressure values comprised between each pair of consecutive data sample numbers; and calculating, by the one or more hardware processors, drift-free plantar pressure parameters in terms of a drift-free Vertical Ground Reaction Force (VGRF) and a 2-dimensional Centre of Pressure (CoP) location for each data sample number falling within each predefined time window w, and using the drift-free plantar pressure parameters to determine walking pattern of the individual for gait monitoring.

13. The method of claim 12, wherein the step of determining a list of pairs of consecutive identified sub-time windows that represent a true stride comprises:

calculating a standard deviation value for each sub-time window ($m_1, m_2, m_3, \ldots, m_n$), based on associated raw 3-axis accelerometer values comprised in the sub-time window;

identifying a sub-list of the sub-time windows having standard deviation values less than a predefined threshold;

calculating a 3-dimensional trajectory for each pair of consecutive identified sub-time windows in the sub-list, based on the associated raw 3-axis accelerometer values and associated raw 3-axis gyroscope values;

determining the trajectory parameters for each pair of the consecutive identified sub-time windows in the sub-list based on an associated 3-dimensional trajectory; and determining the list of pairs of consecutive identified sub-time windows that represent the true stride, wherein associated determined trajectory parameters satisfies:

(i) associated determined trajectory length ranges between predefined upper and lower trajectory length threshold limits;

(ii) associated determined trajectory height ranges between predefined upper and lower trajectory height threshold limits; and (iii) associated determined trajectory foot roll is less than a predefined trajectory foot threshold limit.

14. The method of claim 13, wherein the step of calculating a 3-dimensional trajectory for each pair of consecutive identified sub-time windows comprises:

removing gravity from the raw 3-axis accelerometer values using the associated raw 3-axis gyroscope values to obtain linear acceleration values;

applying the LiTCEM correction method on the linear acceleration values to obtain corrected acceleration values;

integrating the corrected acceleration values over time to determine velocity values;

applying the LiTCEM correction method on the determined velocity values to obtain corrected velocity values; and integrating the corrected velocity values to determine displacement values resulting in the 3-dimensional trajectory for the associated pair of consecutive identified sub-time windows.

15. The method of claim 12, wherein the static pressure value for each raw foot pressure value acquired by each piezoelectric sensor of the plurality of piezoelectric sensors is obtained according to a relation:

$$P_{i,j} = P_{i,(j-1)} + \left(\frac{P_{ijr} + P_{i(j-1)r}}{2}\right)\nabla t$$

wherein i represents a piezoelectric sensor number, j represents a data sample number, $\nabla t$ represents a difference in timestamps for data samples 'j−1' and j, $P_{i,j}$ presents the static pressure value for piezoelectric sensor i and data sample number j, $P_{i,j-1}$ represents the static pressure value for piezoelectric sensor i and previous data sample number 'j−1', $P_{ijr}$ represents the raw foot pressure value for piezoelectric sensor i and data sample number j, and $P_{i(j-1)r}$ represents the raw foot pressure value for piezoelectric sensor i and data sample number 'j−1'.

16. The method of claim 12, wherein the drift-free Vertical Ground Reaction Force (VGRF) is calculated by adding drift-free static pressure values of the plurality of piezoelectric sensors associated with the data sample number.

17. The method of claim 12, wherein the drift-free Vertical Ground Reaction Force (VGRF) for each data sample number j falling within each predefined time window w is calculated according to a relation:

$$VGRF_j = \sum_{i=1}^{N} PC_{ij}$$

wherein i represents a piezoelectric sensor number, N represents number of piezoelectric sensors, j represents a data sample number and $PC_{ij}$ represents the drift-free static pressure value for piezoelectric sensor i and data sample number j.

18. The method of claim 12, wherein the 2-dimensional Centre of Pressure (CoP) location is calculated based on associated drift-free static pressure values, associated drift-free Vertical Ground Reaction Force (VGRF) and locations of associated piezoelectric sensors.

19. The method of claim 12, wherein the 2-dimensional Centre of Pressure (CoP) location for each data sample number j falling within each predefined time window w is calculated according to a relation:

$$CoP_j = \left(\frac{\sum_{i=1}^{N} PC_{ij} * X_i}{VGRF_j}, \frac{\sum_{i=1}^{N} PC_{ij} * Y_i}{VGRF_j}\right)$$

wherein $(X_i, Y_i)$ represents a 2-dimensional location of the piezoelectric sensor i with respect to plane of a sole of a footwear, j represents the data sample number, $PC_{ij}$ represents the drift-free static pressure value for piezoelectric sensor i and data sample number j, $VGRF_j$ represents the drift-free Vertical Ground Reaction Force (VGRF) for the data sample number j.

20. The method of claim 12, wherein the trajectory parameters are used for analyzing at least one of walking speed and angular velocity of the individual.

* * * * *